United States Patent [19]

Toda et al.

[11] Patent Number: 4,769,502
[45] Date of Patent: Sep. 6, 1988

[54] ALKYNOL TYPE COMPOUNDS AND ALCOHOL-SEPARATING PROCESS

[76] Inventors: Fumio Toda, 1431-3, Ushibuchi, Shigenobu-cho, Onsen-gun, Ehime 791-02; Koichi Tanaka, 4-2-2, Tarumi, Matsuyama-shi, Ehime 790, both of Japan

[21] Appl. No.: 48,495

[22] Filed: May 8, 1987

Related U.S. Application Data

[63] Continuation of Ser. No. 810,366, filed as PCT JP85/00147 on Mar. 26, 1985, published as WO85/04394 on Oct. 10, 1985, abandoned.

Foreign Application Priority Data

Mar. 26, 1984 [JP] Japan .................................. 59-59221
Mar. 26, 1984 [JP] Japan .................................. 59-59222

[51] Int. Cl.⁴ ...................... C07C 27/26; C07C 29/74; C07C 33/28
[52] U.S. Cl. .................................. 568/810; 568/809; 568/854; 568/868; 568/913
[58] Field of Search ............... 568/809, 780, 810, 854, 568/868, 913

[56] References Cited

U.S. PATENT DOCUMENTS

| | | | |
|---|---|---|---|
| 3,082,216 | 3/1963 | Dimroth et al. | 568/809 |
| 4,467,102 | 8/1984 | Toda et al. | 568/809 |

FOREIGN PATENT DOCUMENTS

| | | | |
|---|---|---|---|
| 0216841 | 12/1984 | Japan | 568/809 |
| 0011435 | 1/1985 | Japan | 568/809 |
| 0000147 | 12/1985 | PCT Int'l Appl. | 568/809 |

OTHER PUBLICATIONS

Yamada, "Tetrahedron Letters", No. 22(1981), pp. 3865-3872, Pergamon Press GB.
Toda, "Tetrahedron Letters", No. 33(1968), pp. 3695-3698), 3736-3737, Pergamon Press, GB.
Tanaka et al, "J. Chem. Soc., Chem. Comm.", (1983), pp. 593-594.
Koftry, "J. Org. Chem", vol. 50(1985), pp. 2154-2158.
"Gendai Kagaku, No. 155, pp. 24-31 (Feb. 1984).

*Primary Examiner*—Werren B. Lone
*Attorney, Agent, or Firm*—Wolder, Gross & Yavner

[57] ABSTRACT

Alkynol type compounds of the following formula (I):

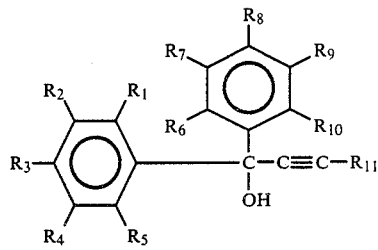

[wherein $R_1$–$R_5$ and $R_6$–$R_{10}$ each represent hydrogen atoms or lower alkyl group and $R_{11}$ represents a lower alkyl group or a group of the formula:

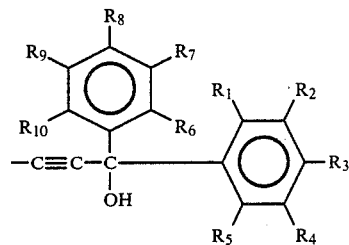

(wherein $R_1$–$R_5$ and $R_6$–$R_{10}$ are as hereinbefore defined); at least one of $R_1$–$R_5$ and at least one of $R_6$–$R_{10}$ being lower alkyl grops.] These compounds are capable of forming and precipitating crystalline complexes with alcohols when added to an aqueous solution of alcohol. Thus, these compounds are useful for separating alcohols from aqueous solutions of alcohols.

9 Claims, 1 Drawing Sheet

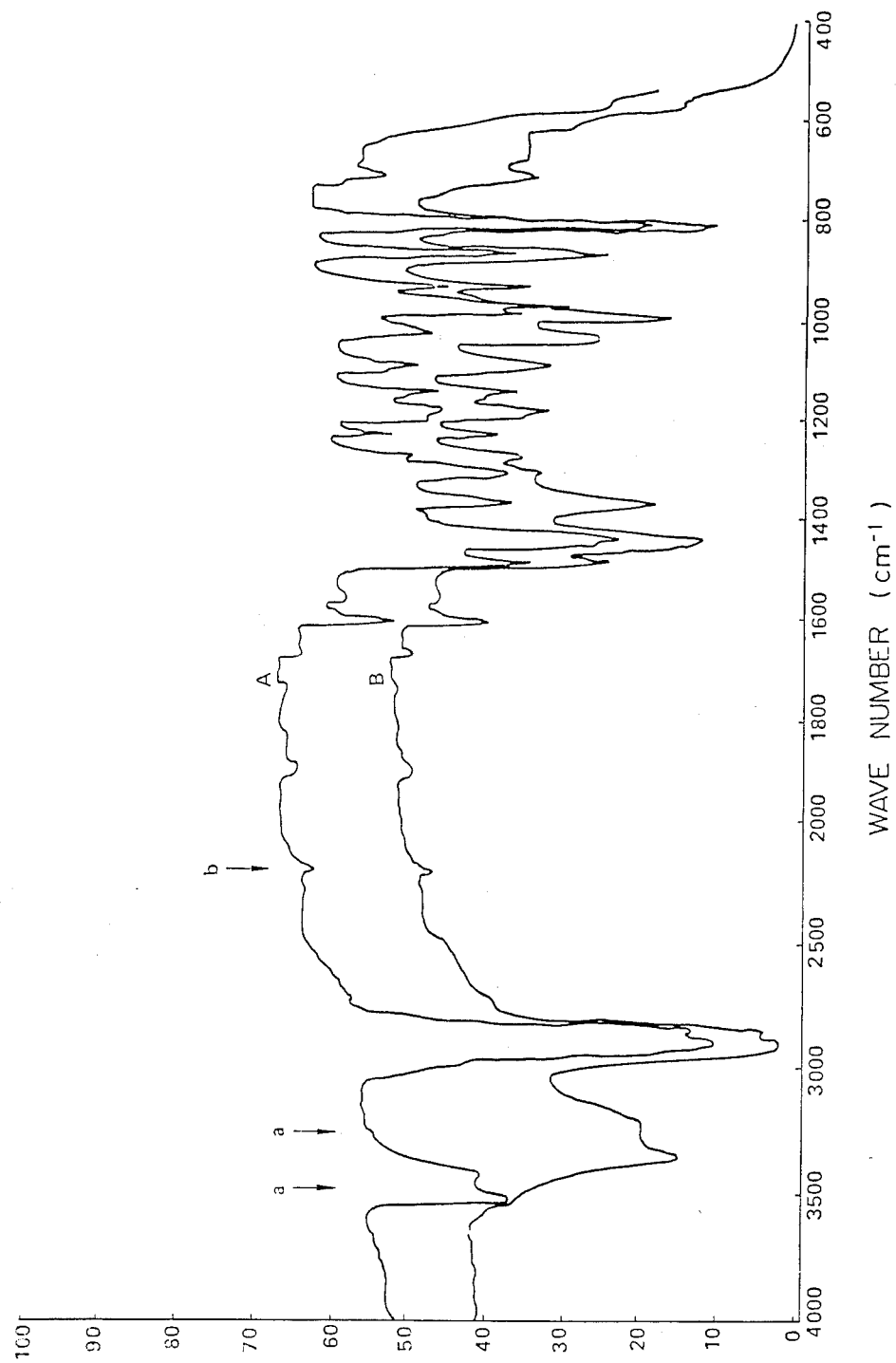

ALKYNOL TYPE COMPOUNDS AND ALCOHOL-SEPARATING PROCESS

This application is a continuation, of application Ser. No. 810,366, filed as PCT JP85/00147 on Mar. 26, 1985, published as WO85/04394 on Oct. 10, 1985, now abandoned.

TECHNICAL FIELD

The present invention relates to alkynol type compounds and alcohol-separating agents. The term "alcohol-separating agent" used herein denotes a compound, which, when added to an aqueous solution of alcohol, precipitates crystals of a complex with with the alcohol, thereby to separating the alcohol.

BACKGROUND OF THE ART 9-(1-propynyl)-9-hydroxyquinone represented by the formula:

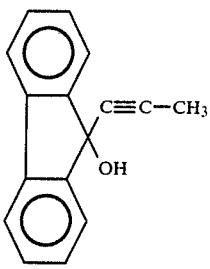

and 2,5-bis(2,4-dimethylphenyl) hydroquinone were previously known as acetylene-type compounds capable of forming a complex with an alcohol in an aqueous alcoholic solution such as aqueous ethanol solution, [with reference to a report entitled "Specific compounds capable of recognizing molecules" in the Abstract of lectures at the Joint Meeting in The Autumn Session of The 38th Annual Meeting of The Chemical Society of Japan (including the combined forum), Announcement Meeting of Kagaku-kankei Rengo-kyokai and Autumn Session of Chubu Kagaku-kankei Kyokai-shibu-rengo, published by The Chemical Society of Japan, a corporate juridical body (1978) and Chemical Letters, pp. 1699–1702 (1983), published by The Chemical Society of Japan.]

DISCLOSURE OF THE INVENTION

The present invention relates to alkynol compounds and alcohol-separating agents comprising the same.

The present invention provides an alkynol type compound of the formula (I):

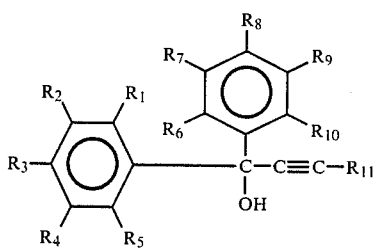

[wherein $R_1$–$R_5$ and $R_6$–$R_{10}$ each represent hydrogen atoms or lower alkyl groups, and $R_{11}$ is a lower alkyl group or a group of the formula:

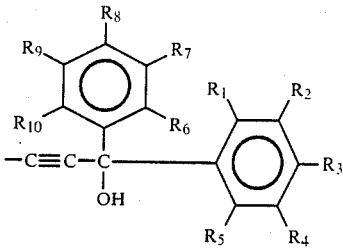

(wherein $R_1$–$R_5$ and $R_6$–$R_{10}$ are as hereinbefore defined)]; and at least one of $R_1$–$R_5$ and at least one of $R_6$–$R_{10}$ being lower alkyl groups) (the compound is hereinafter referred to as Compound (I) and compounds of other formulae are similarly designated)], and an agent for separting alcohol from water-containing alcohol solution, comprising Compound (I).

Compounds (I) are capable of forming complexes with various alcohols. In the definition of both $R_1$–$R_5$ and $R_6$–$R_{10}$ of the formula (I), the lower alkyl group include, for example, straight or branched alkyl groups having 1–4 carbon atoms such as, e.g. methyl, ethyl, n-propyl, i-propyl, n-butyl and i-butyl, sec-butyl, tert-butyl, n-pentyl and n-hexyl groups. With respect to ease of formation of the complexes and to their stability, it is preferred to use Compounds (I) wherein $R_1$ is a lower alkyl, at least one of $R_2$–$R_4$ is a lower alkyl, $R_5$ is a hydrogen atom, at least one of $R_6$–$R_{10}$ is a lower alkyl group and at least one of $R_6$–$R_{10}$ is a a hydrogen atom. Especially good results may be given by Compounds (I) wherein $R_6$ is a lower alkyl group and $R_{10}$ is a hydrogen atom. In the definition of $R_{11}$ in the formula (I), the lower alkyl group is exemplified by straight and branched alkyl groups having 1–6 carbon atoms such as e.g. methyl, ethyl, n-propyl, i-propyl, n-butyl, i-butyl, sec-butyl, tert-butyl, n-pentyl and n-hexyl groups.

Methods of producing Compounds (I) are classified into two cases. In one case, $R_{11}$ is a lower alkyl group, and in another case, $R_{11}$ is a 3,3-diaryl-3-hydroxy-1-propyn-1-yl group, as described in the following. Preparation of Compounds (I) wherein $R_{11}$ is a lower alkyl group (hereiafter referred to as Compounds (I-1):

Compound (I-1) may be prepared by reaction of a compound of the following formula (II):

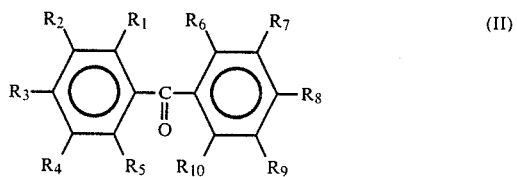

(wherein $R_1$–$R_{10}$ are as hereinbefore defined) with a compound of the formula (III):

$$HC{\equiv}C\text{-}R_{12} \qquad (III)$$

(wherein $R_{12}$ represents a lower alkyl group mentioned in the definition of $R_{11}$) in a liquid ammonia in the presence of sodium amide.

In order to dissolve Compounds (II) and (III), a small amount of a solvent such as tetrahydrofuran and ethyl ether may be used. The reaction may preferably be carried out at a temperature of from about −45° C. to −65° C. After completion of the reaction, ammonia is removed from the reaction solution by evaporation. The reaction solution is neutralized with a mineral acid such as hydrochloric acid. Compound (I-1) may be obtained by extraction with a solvent (e.g. ethyl ether) which is capable of dissolving Compounds (I-1) but has a poor compatibility with water, followed by removal of the solvent from the extracted solution by evaporation. Preparation of Compounds (I) wherein $R_{11}$ is a 3,3-diaryl-3-hydroxy-1-propyn-1-yl group (hereinafter referred to as Compounds (I-2)):

Compound (I-2) may be prepared by a process comprising the following two steps.

In the first step, a compounds of the formula (IV):

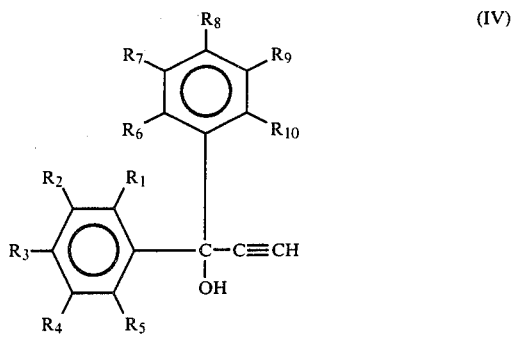

(wherein $R_1$–$R_{10}$ are as hereinbefore defined) is prepared by reaction of a Compound (II) with acetylene in liquid ammonia in the presence of sodium amide. The reaction, the isolation and the purification of Compound (IV) after completion of reaction may be carried out in a similar manner to that applied to the preparation and purification of the above-mentioned Compounds (I-1).

Subsequently, Compound (IV) is kept in an inert solvent in the presence of cuprous chloride as catalyst, and in the presence of a base. The reaction may be effected under a stream of air or oxygen to obtain Compound (I-2). The inert solvents which may be used for this purpose are exemplified by ketones such as acetone, ethyl methyl ketone and the like. The bases which may be used for this purpose are exemplified by tertiary amines such as pyridine, triethylamine and the like. The reaction may conveniently be effected at room temperature, although it is possible, if desired, to carry out the reaction at an elevated temperature. After completion of reaction, the reaction solution, with or without concentration, is poured into a mineral acid such as hydrochloric acid to obtain crystals of Compound (I-2).

Compounds (I) form complexes with alcohols in aqueous solutions containing various alcohols. The resultant complexes may precipitate in the form of crystals since their water-solubility is generally low. The crystals are separated from the liquid phase and then washed and dried. Alcohol can be liberated by heating the crystals, and a pure alcohol or an alcohol having a very high purity may be obtained. The residual solid represents Compound (I) which may then be reused.

Such alcohols are exemplified by lower alkanols, aliphatic unsaturated alcohols (e.g. allyl alcohol, crotyl alcohol, propargyl alcohol etc.), alicyclic alcohols (e.g. cyclopentanol, cyclohexanol etc.), aromatic alcohols (e.g. benzyl alcohol, cinnamyl alcohol etc.), heterocyclic alcohols (e.g. furfuryl alcohol etc.), lower alkylene glycols, lower alkane triols, lower alkane tetrols and the like.

The above-mentioned lower alkanols are exemplified by straight and branched alkanols having 1–6 carbon atoms such as methanol, ethanol, n-propanol, i-propanol, n-butanol, i-butanol, sec-butanol, tert-butanol, n-pentanol, n-hexanol and the like.

Examples of the lower alkylene glycols which may be used for the purpose of the invention include straight and branched alkylene glycols having 1–6 carbon atoms such as ethylene glycol, trimethylene glycol, propylene glycol, 1,3-butanediol, 1,4-butanediol and the like. Preferred examples of alkane triols include straight and branched alkane triols having 1–6 carbon atoms such as glycerine and the like. Examples of preferred lower alkane tetrols include straight and branched alkane tetrols having 1–6 carbon atoms such as pentaerythritol and the like.

Although the concentration of alcohol contained in the aqueous alcohol solution which is placed in contact with Compounds (I), may be variable, usually a concentration of more than 5% (particularly, more than 30%) for Compounds (I) and a concentration of more than 30% (particularly more than 70%) for Compounds (I-2) are preferable.

The aqueous alcohol solutions which may be used for the purpose of this invention are exemplified by alcohol fermentation broth, reaction mixture of alcohol synthesis and the like.

With regard to the method of contacting, it is possible to add Compounds (I) directly to an aqueous solution of alcohol. However, in general, better results may be obtained by dissolving or melting Compounds (I) by heating. It is also possible to dissolve Compounds (I) in a small amount of a solvent such as e.g. ether, followed by mixing the solution with the aqueous solution of alcohol.

After placing Compound (I) into contact with an aqueous alcohol, the mixture is left at ambient or cold temperature to form the crystals of complex at a ratio of 1:1 calculated on the basis of the number of hydroxide group. The precipitated crystals are separated and heated to a suitable temperature which is higher than the boiling point of the desired alcohol. In this manner, the alcohol is separated.

In general, the complexes formed with Compounds (I) and the alcohols have a high stability so that no substantial loss occurs during the separation and subsequent drying. Usually, Compounds (I-1) and (I-2) are highly soluble in the alcohol solution as their solubilities are more than 30% and more than 70% respectively. Thus, it is readily possible to form the desired complexes.

BRIEF DESCRIPTION OF THE DRAWINGS

FIG. 1 shows the IR values (by Nujol method) of Compound 1 as well as of crystals of a complex formed with Compound 1 and ethanol at a mol. ratio of 1:1. The symbols used in this figure denote the following:

A: Compound 1,
B: Said complex
a: Absorption due to O-H stretching,
b: Absorption due to acetylene bond.

BEST MODE FOR CARRYING OUT THE INVENTION

The following examples illustrate the invention.

EXAMPLE 1

0.5 g of $Fe(NO_3)_3.9H_2O$ and 49 g of sodium are added to liquid ammonia (1.5 l) to obtain sodium amide. The reaction mixture is cooled to a temperature of $-40°$ C. to $-65°$ C. with dry ice-methanol. A mixture of equal amounts of propylene dichloride (80 g) and anhydrous ether is added dropwise to the reaction solution with stirring. After further stirring for one hour, an anhydrous tetrahydrofuran solution of di-(2,4-dimethlphenyl) ketone (140 g) is dropwise added to the reaction solution while cooling and stirring. The reaction solution is further stirred for 2 hours and is then left at ambient temperature overnight. After removal of ammonia from the reaction mixture by evaporation, 300 ml of 3N diluted HCl is added to the reaction solution, followed by extraction with ether.

The ether layer is washed with water and dried. Ether is removed from the extract by evaporation to obtain 1,1-bis(2,4-dimethylphenyl)-2-butyn-1-ol (hereinafter referred to as. Compound 1) is obtained as a colorless oily product. By adding 80% ehtanol (about 50 ml ) to Compound 1, cystals of a complex are preciptated which contain Compound 1, and ether at a molar ratio of 1:1 (colourless prism crystals having a melting point of 64°-65° C.). The resultant crystals of the complex are recovered by filtration and dried under reduced pressure (about 20 mmHg) at a temperature of about 60° C. for 5 hours, where by COmpound 1 (120 g) in the form of white powders is obtained.

Melting point: 83°-85° C.,

IR (Nujol method): as shown in FIG. 1 wherein A and B denote respectively Compound 1 and the above-mentioned complex.

EXAMPLE 2

Compound 1 (7.6 g) is melted in 2 ml of 80% (v/v) ethanol by heating. The solution is left at ambient temperature for 2 hours to precipitate crystals which are then collected by filtration and dried under reduced pressure (20 mmHg) at room temperature for 30 minutes to obtain colourless prism crystals of a complex formed between Compound 1 and ethanol (1:1, 8.7 g). Ethanol (0.98 g) is obtained by heating the crystals (8.7 g) to about 100° C.

EXAMPLE 3

Compound 1 (2.0 g) is melted in 1.68 ml of 50% v/v ethanol by heating. The resultant mixture is left at room temperature for 2 hours to precipitates crystals which are then treated in a similar manner to that described in Example 2 to obtain 2.3 g of a complex formed between Compound 1 and ethanol (1:1). 0.26 g of ethanol is liberated.

EXAMPLE 4

2.0 g of Compound 1 is melted in 3.57 ml of 35% (v/v) ethanol by heating. The mixture is left at room temperature for 12 hours to obtain 2.3 g of crystals of the complex formed between Compound 1 and ethanol (1:1).

EXAMPLE 5

0.5 g of $Fe(NO_3)_3.9H_2O$ and 49 g of sodium are added to liquid ammonia (1.5 ) to produce sodium amide. Then acetylene gas is introduced into the reaction mixture at a temperature of $-40°$ C. to $-65°$ C. (whilst cooling using dry ice-methanol) for one hour while stirring. Then, an anhydrous tetrahydrofuran solution containing 476 g of di-(2,4-dimethylphenyl) ketone is added dropwise to the reaction mixture while cooling and stirring. After further stirring for 2 hours, the mixture is left at room temperature overnight. After removal of ammonia from the reaction solution by evaporation, 3N diluted HCl (300 ml) is added to the solution. After extraction with ether, the ether layer is washed with water and dried. After removal of ether by evaporation, 1,1-bis(2,4-dimethylphenyl)-2-propyn-1-ol is obtained as colourless oily product with a yield of 450 g.

The 1,1-bis(2,4-dimethylphenyl)-2-propyn-1-ol (450 g) is dissolved in acetone (1 l). Cuprous chloride (50 g) and pyridine (100 ml) are added to the reaction solution, which is then stirred overnight under a stream of oxygen. The raction mixture is poured into 1 liter of 3N-HCl to obtain 1,1,6,6-tetra(2,4-dimethylphenyl)-2,4-dexadyne-1,6-diol (hereinafter referred to as Compound 2) in the form of white crystals (yield: 400 g, melting point: 198 C.).

EXAMPLE 6

Compound 2 (1.0 g) is dissolved in 50 ml of 95% ethanol by heating. The mixture is left at room temperature for 12 hours to obtain 1.1 g of a complex formed between Compound 2 and ethanol (molar ratio 1:2) in the form of colourless prism crystals. The melting point of the product is indefinite. 0.13 g of ethanol is obtained by heating 1.1 g of the resultant crystals at about 100° C.

We claim:

1. Alkynol type compounds of the following formula (I):

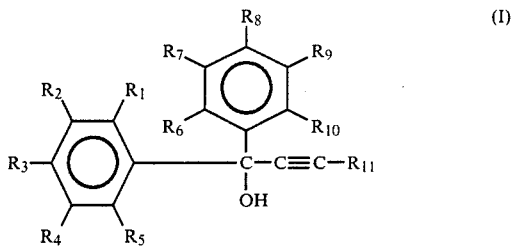

[wherein $R_1$–$R_5$ and $R_6$–$R_{10}$ each represent hydrogen atoms or lower alkyl group and $R_{11}$ represents a lower alkyl group or a group of the formula:

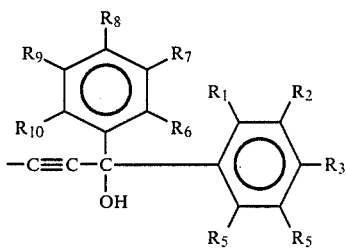

(wherein $R_1$–$R_5$ and $R_6$–$R_{10}$ are as hereinbefore defined), at least one of $R_1$–$R_5$ and at least one of $R_6$–$R_{10}$ being lower alkyl groups].

2. 1,1-bis (2,4-dimethylphenyl)-2-butin-1-ol.

3. 1,1,6,6-tetra(2,4-dimethylphenyl)-2,4-hexadyne-1, 6-diol.

4. A process for separating an alcohol from an aqueous solution containing said alcohol which comprises forming a complex of a compound of claim 1 with said alcohol in said solution, isolating the resultant complex from said solution, and recovering said alcohol therefrom.

5. A process for separating an alcohol as claimed in claim 4 wherein $R_1$ is a lower alkyl group; at least one member of $R_2$–$R_4$ is a lower alkyl group; at least one of $R_6$–$R_{10}$ is a lower alkyl group; and at least one of $R_6$ and $R_{10}$ is a hydrogen atom.

6. A process for separating an alcohol as claimed in claim 4 wherein $R_6$ is a lower alkyl group and $R_{10}$ is a hydrogen atom.

7. A process for separation of alcohol as claimed in claim 4, wherein said alcohol to be separated is selected from lower alkanols, allyl alcohol, crotyl alcohol, propargyl alcohol, cyclopentanol, cyclohexanol, benzyl alcohol, cinnamyl alcohol, furfuryl alcohol, lower alkylene glycols, lower alkane triols and lower alkane tetrols.

8. The process of claim 4, wherein said compound is selected from the group consisting of 1,1-bis(2,4-dimethyl-phenyl) -2-butin-1-ol and 1,1,6,6- tetra(2,4-dimethyl-phenyl)-2,4-hexadyne-1,6-diol.

9. The process of claim 4, wherein said alcohol is ethanol.

* * * * *